US00PP20847P3

(12) United States Plant Patent
Eremin

(10) Patent No.: US PP20,847 P3
(45) Date of Patent: Mar. 16, 2010

(54) ***PRUNUS* ROOTSTOCK NAMED 'MYROCOT'**

(50) Latin Name: *Prunus cerasifera×armeniaca*
Varietal Denomination: Myrocot

(75) Inventor: Gennadiy Eremin, Krasnodar (RU)

(73) Assignee: Varieties International, LLC, Dundee, OR (US)

( * ) Notice: Subject to any disclaimer, the term of this patent is extended or adjusted under 35 U.S.C. 154(b) by 0 days.

(21) Appl. No.: 12/218,621

(22) Filed: Jul. 16, 2008

(65) Prior Publication Data

US 2010/0017925 P1 Jan. 21, 2010

(51) Int. Cl.
*A01H 5/00* (2006.01)

(52) U.S. Cl. ..... Plt./180

(58) Field of Classification Search ..... Plt./183, Plt./180

See application file for complete search history.

*Primary Examiner*—June Hwu
(74) *Attorney, Agent, or Firm*—The Webb Law Firm

(57) ABSTRACT

A new and distinct *Prunus cerasifera×armeniaca* plant used as a rootstock for plum and apricot varieties that exhibits desirable propagation characteristics and white flowers.

2 Drawing Sheets

Botanical classification: *Prunus cerasifera×armeniaca.*
Varietal denomination: 'Myrocot'.

BACKGROUND OF THE INVENTION

The present invention comprises a new and distinct cultivar of *Prunus cerasifera×armeniaca* used as a rootstock known by the varietal name 'Myrocot'. The new variety was discovered in the Krasnodar region of Russia in 1997. The new variety is the result of planned breeding between *Prunus cerasifera* Seedling No. 3 (female parent, unpatented) and an unnamed *Prunus armeniaca* plant (male parent, unpatented). The new variety is similar to *Prunus pumila×armeniaca* 'Druzba' (unpatented) in leaf form and length, as well as fruit characteristics. 'Myrocot' has thinner one-year-old shoots than 'Druzba'. The purpose of breeding 'Myrocot' was to provide adaptive, clonal rootstocks of semi-dwarf type vigor. The new variety has been trial and field tested and has been found to retain its distinctive characteristics and remain true to type through successive propagations. The following characteristics distinguish 'Myrocot' from other varieties known to the breeder:

1. The morphology is intermediate between myrobalan and apricot;
2. High temperature and frost tolerance;
3. Easy to propagate by cuttings;
4. Plum compatible;
5. Developed root system; and
6. Resistant to root and leaf diseases.

Comparison information of 'Myrocot' to its parents is not available, as both parents no longer exist. However, *Prunus cerasifera* varieties are generally not compatible for use as a rootstock with apricot varieties, while 'Myrocot' is compatible with apricot varieties. Further, *Prunus cerasifera* varieties are generally more vigorous and larger than 'Myrocot'. Additionally, Prunus armeniaca varieties are generally not compatible for use as a rootstock with plum varieties, while 'Myrocot' is compatible with plum varieties. Also, *Prunus armeniaca* varieties are more vigorous than 'Myrocot'.

DESCRIPTION OF THE DRAWINGS

The accompanying photographic drawings illustrate the new variety, with the color being as nearly true as is possible with color illustrations of this type.

Figure 1:
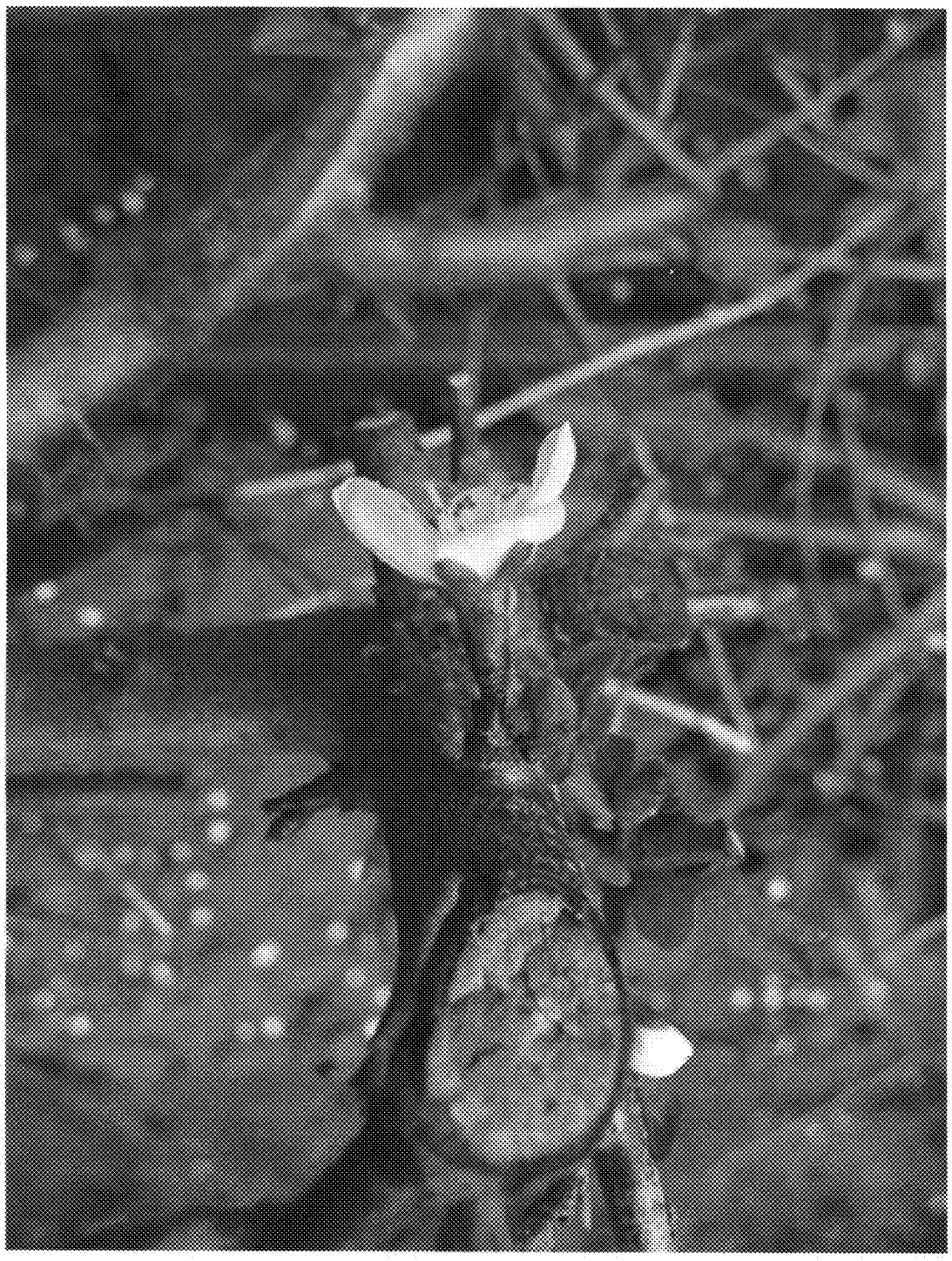
FIG. 1 shows the new variety grown to a flowering plant.
Figure 2:
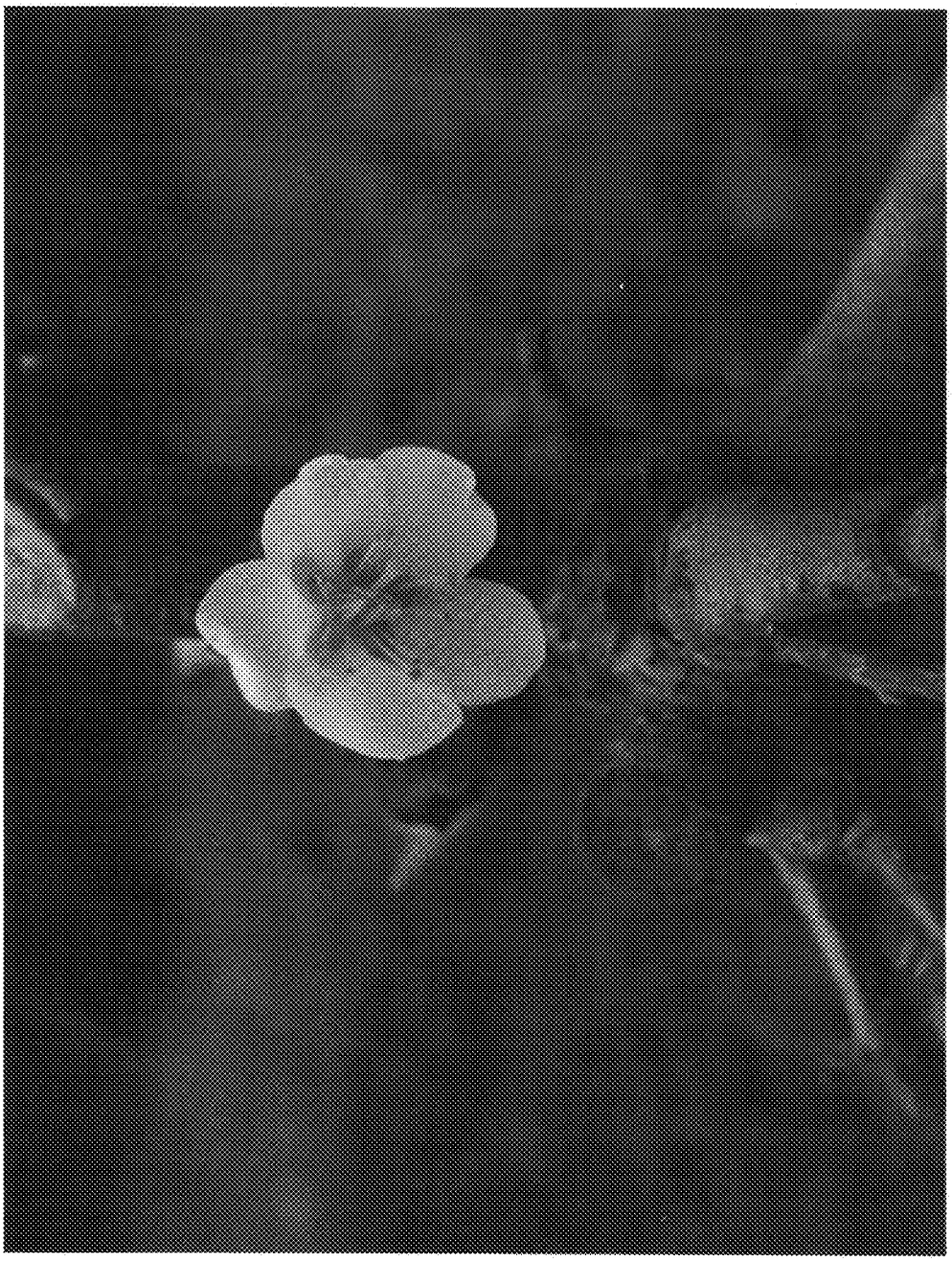
FIG. 2 shows a close-up view of petals of the new variety.

The photographic drawings were taken of a 5 year-old 'Myrocot' plant in Oregon that is pruned to the ground yearly.

DETAILED BOTANICAL DESCRIPTION

The following detailed description sets forth the characteristics of the new cultivar. The data which defines these characteristics were collected by asexual reproductions via meristem inoculation, and cuttings carried out in the Krasnodar Region of Russia. The new variety was grown under standard apricot growing conditions outdoors in Russia. The color readings were taken in natural daylight, and the plant was 10 years old when described. Color references are primarily to the 1995 R.H.S. Colour Chart of The Royal Horticultural Society of London.

Tree:
Size:
*Height.*—3.5 m.
*Spread.*—2.0 m.
Vigor: Medium.
Form: Rounded.
Bearing: No fruit observed to date.
Density: Medium.
Pathogen resistance:
*Fungal disease.*—Stable.
*Insects.*—Susceptible to leaf insects.
*Mites.*—Tolerant.
*Viruses.*—Tolerant.
*Other diseases.*—Tolerant to bacterial disease.
Rootstock performance:
*Root sprouts (suckering).*—None.
*Anchorage.*—Very well.

*Compatibility.*—Good with plum and apricot.
*Vigor.*—Medium.

Trunk:
*Size.*—16 cm. at approximately 25 cm. from the ground.
*Bark color.*—200C.
*Surface texture.*—Smooth.
*Lenticels.*—Length: 2.5 cm. Color: 198B. Density: High.

Branches:
*Diameter.*—0.4 cm.
*Surface texture.*—Smooth, no pubescence present.
*Color.*—177B.
*Average angle.*—26°.
*Lenticels.*—Length: 1.5 cm. Width: 0.5 cm. Density: Dense. Color: 200A. Shape: Small and rounded early in growth; on older bark, the lenticels are elongated and numerous.

Leaves:
*Length.*—4.8 cm.
*Width.*—3.7 cm.
*Form.*—Oval.
*Base.*—Acute.
*Apex.*—Obtuse/acute.
*Margin.*—Serrate.
*Pubescence.*—Upper surface: Almost absent. Lower surface: Little present.
*Color.*—Young leaves: Upper surface: 211C. Lower surface: 198A. Mature leaves: Upper surface: 198A. Lower surface: 189C.
*Petiole.*—Length: 3 cm. Color: 135B. Surface texture: Smooth.
*Veins.*—Venation type: Medium. Color: Upper surface: 211C. Lower surface: 135C.

Flower buds:
*First bud burst.*—Approximately mid-April in Oregon, but varies by region.
*Pedicel.*—Length: 2.5 cm. Diameter: 1 cm. Color: 144B.
*Bud.*—Length: 2 cm. Width: 3.5 cm. Color: 200A.

Flowers:
*Blooming period.*—April 5–April 15 in the Krasnodar region of Russia.
*Pollination requirements.*—Autofertile.
*Number of flowers per raceme.*—3.
*Fragrance.*—Weak.
*Petals.*—Number: 5. Length: 4.5 cm. Width: 3.7 cm. Shape: Cupped. Aspect: Flat. Margin: Entire.
*Color.*—When opening: Upper surface: 155C. Lower surface: 155C. Fully opened: Upper surface: 155C. Lower surface: 144D.
*Sepals.*—Shape: Oval. Margin: Entire. Length: 3.5 mm. Width: 3.5 mm.
*Color.*—Upper surface: 201C. Lower surface: 201C.
*Stamens.*—Number (per flower): 12.
*Anthers.*—Shape: Rounded. Length: 1 mm. Color: 22A.
*Pollen.*—Color: 9A. Amount (generally): Plentiful.
*Pistils.*—Average number: 5. Length: 1.8 mm.
*Style.*—Length: Medium. Color: 9A.
*Stigma.*—Shape: Reniform. Color: 9A.

Fruit:
*Size.*—Diameter: Small; 3.5 to 4.0 cm. Length: 3.5 cm.
*Skin.*—Thickness: Fine. Texture: Soft. Tendency to crack: Strong. Color: 201C. Ground color: 21A.
*Flesh.*—Aroma: Weak. Color: 21A. Texture: Soft. Eating quality: Fair.
*Seeds.*—Number per fruit: 1. Length: 1.6 cm. Breadth: 1.2 cm. Form: Oval. Color: 164B.
*Stem.*—Length: 1.5–2.0 cm. Width: 2 mm. Color: 136C.

Tree winter hardiness: USDA Hardiness Zone 4.
Bud winter hardiness: USDA Hardiness Zone 4.
Drought tolerance: High.
Insect resistance: Nematode resistance.
Disease resistance: No particular disease resistance observed to date.
Multiplication ability: The new variety may be multiplied by hardwood cuttings, softwood cuttings, and micropropagation (tissue culture).
Soil adaptation and tolerance: Moderate tolerance to chlorosis and adapts to most soil types (light to heavy soils).
Yield efficiency: Above average yield efficiency for both apricot and plum scions.

I claim:

1. A new and distinct variety of *Prunus cerasifera×armeniaca* plant, as herein illustrated and described.

* * * * *